US011627243B2

(12) United States Patent
Reddy et al.

(10) Patent No.: US 11,627,243 B2
(45) Date of Patent: Apr. 11, 2023

(54) HANDHELD WIRELESS ENDOSCOPE IMAGE STREAMING APPARATUS

(71) Applicant: Phaox LLC, Yardley, PA (US)

(72) Inventors: Nishant Reddy, Yardley, PA (US); Amit Patel, Providence, RI (US); Michael Pfisterer, Lafayette, CA (US); Alejandro Vazquez, Pawtucket, RI (US); Trevor Pennypacker, Menlo Park, CA (US)

(73) Assignee: Phaox LLC, Yardley, PA (US)

( * ) Notice: Subject to any disclaimer, the term of this patent is extended or adjusted under 35 U.S.C. 154(b) by 0 days.

(21) Appl. No.: 17/726,526

(22) Filed: Apr. 21, 2022

(65) Prior Publication Data

US 2023/0023904 A1 Jan. 26, 2023

Related U.S. Application Data

(60) Provisional application No. 63/225,440, filed on Jul. 23, 2021.

(51) Int. Cl.
*H04N 5/232* (2006.01)
*A61B 1/00* (2006.01)
*H04N 5/225* (2006.01)
*A61B 1/06* (2006.01)

(52) U.S. Cl.
CPC ..... *H04N 5/23206* (2013.01); *A61B 1/00006* (2013.01); *A61B 1/00016* (2013.01); *A61B 1/00055* (2013.01); *A61B 1/00147* (2013.01); *A61B 1/06* (2013.01); *H04N 5/2256* (2013.01); *H04N 2005/2255* (2013.01)

(58) Field of Classification Search
CPC ........................ A61B 1/00016; H04N 5/23206
USPC ........................................................... 345/350
See application file for complete search history.

(56) References Cited

U.S. PATENT DOCUMENTS

| | | | | | |
|---|---|---|---|---|---|
| 4,633,304 | A | * | 12/1986 | Nagasaki | H04N 7/183 348/69 |
| 5,005,559 | A | * | 4/1991 | Blanco | A61B 1/00147 600/117 |
| 5,627,584 | A | * | 5/1997 | Nishikori | A61B 1/123 348/72 |
| 5,638,819 | A | * | 6/1997 | Manwaring | A61B 5/06 600/117 |
| 5,879,289 | A | * | 3/1999 | Yarush | A61B 1/00042 600/179 |
| 6,141,037 | A | * | 10/2000 | Upton | A61B 1/00016 348/69 |
| 6,436,107 | B1 | * | 8/2002 | Wang | A61B 34/75 606/139 |
| 7,030,904 | B2 | * | 4/2006 | Adair | A61B 1/00135 348/E3.019 |

(Continued)

*Primary Examiner* — John P Leubecker
*Assistant Examiner* — Jae Woo
(74) *Attorney, Agent, or Firm* — Cognition IP, P.C.; Edward Steakley

(57) ABSTRACT

Methods, systems, and apparatus, including computer programs encoded on computer storage media relate to a handheld wireless endoscope image streaming apparatus. The apparatus may establish a wireless connection to a computer system. The apparatus may obtain, via a digital camera, video imagery via an endoscope, the video imagery including multiple frames. The apparatus may stream to a computer system video data.

18 Claims, 15 Drawing Sheets

(56) References Cited

U.S. PATENT DOCUMENTS

| | | | | |
|---|---|---|---|---|
| 7,048,686 B2* | 5/2006 | Kameya | | A61B 1/05 600/179 |
| 8,213,698 B2* | 7/2012 | Wang | | A61B 5/073 600/101 |
| 10,499,792 B2* | 12/2019 | Law | | A61B 1/04 |
| 10,595,887 B2* | 3/2020 | Shelton, IV | | A61B 18/16 |
| 2002/0013512 A1* | 1/2002 | Sendai | | A61B 1/043 600/118 |
| 2002/0013513 A1* | 1/2002 | Bala | | A61B 1/042 600/178 |
| 2002/0022763 A1* | 2/2002 | Sano | | G02B 23/2484 348/E5.029 |
| 2002/0099263 A1* | 7/2002 | Hale | | A61B 1/00147 600/117 |
| 2005/0219205 A1* | 10/2005 | Bailey | | G06F 3/016 345/156 |
| 2006/0293563 A1* | 12/2006 | Banik | | G16Z 99/00 600/117 |
| 2007/0083083 A1* | 4/2007 | Mori | | A61B 1/00016 600/118 |
| 2007/0203396 A1* | 8/2007 | McCutcheon | | A61B 1/00148 600/173 |
| 2009/0018395 A1* | 1/2009 | Honda | | A61B 1/041 600/118 |
| 2009/0209810 A1* | 8/2009 | Endo | | A61B 1/00016 600/109 |
| 2009/0237498 A1* | 9/2009 | Modell | | G02B 27/46 348/E7.085 |
| 2010/0046816 A1* | 2/2010 | Igual-Munoz | | G06T 7/12 382/128 |
| 2010/0076263 A1* | 3/2010 | Tanaka | | A61B 1/0051 600/109 |
| 2011/0018988 A1* | 1/2011 | Kazakevich | | G02B 23/2484 348/E7.085 |
| 2011/0082334 A1* | 4/2011 | Dolt | | A61B 1/045 600/104 |
| 2011/0301447 A1* | 12/2011 | Park | | A61B 1/000096 600/407 |
| 2012/0162401 A1* | 6/2012 | Melder | | H04N 7/183 348/E7.085 |
| 2012/0327186 A1* | 12/2012 | Kitamura | | A61B 6/5247 348/45 |
| 2013/0023730 A1* | 1/2013 | Kitamura | | A61B 1/0005 600/104 |
| 2013/0204085 A1* | 8/2013 | Alexander | | A61B 1/00158 600/101 |
| 2014/0107471 A1* | 4/2014 | Haider | | A61B 5/1076 606/82 |
| 2014/0194896 A1* | 7/2014 | Frimer | | A61B 1/00006 606/130 |
| 2015/0011830 A1* | 1/2015 | Hunter | | A61B 1/0016 600/118 |
| 2016/0302653 A1* | 10/2016 | Inoue | | A61B 1/00009 |
| 2017/0027650 A1* | 2/2017 | Merck | | A61B 1/045 |
| 2018/0110398 A1* | 4/2018 | Schwartz | | A61B 1/00006 |
| 2018/0177390 A1* | 6/2018 | Iannitti | | A61B 1/3132 |
| 2018/0196251 A1* | 7/2018 | Duckett, III | | A61B 1/00188 |
| 2018/0309828 A1* | 10/2018 | Ghabour | | H04L 45/126 |
| 2018/0368926 A1* | 12/2018 | Wade | | H04L 65/75 |
| 2019/0059942 A1* | 2/2019 | Watson | | A61B 17/3421 |
| 2019/0201029 A1* | 7/2019 | Shelton, IV | | G16H 30/40 |
| 2019/0274523 A1* | 9/2019 | Bates | | A61B 1/00059 |
| 2019/0328217 A1* | 10/2019 | Moreau | | A61B 1/05 |
| 2019/0374095 A1* | 12/2019 | Lord | | A61B 1/053 |
| 2020/0380718 A1* | 12/2020 | Schoch | | A61B 1/00193 |
| 2020/0397228 A1* | 12/2020 | Heni | | A61B 1/00018 |
| 2022/0148128 A1* | 5/2022 | Ogura | | G06F 3/0346 |

* cited by examiner

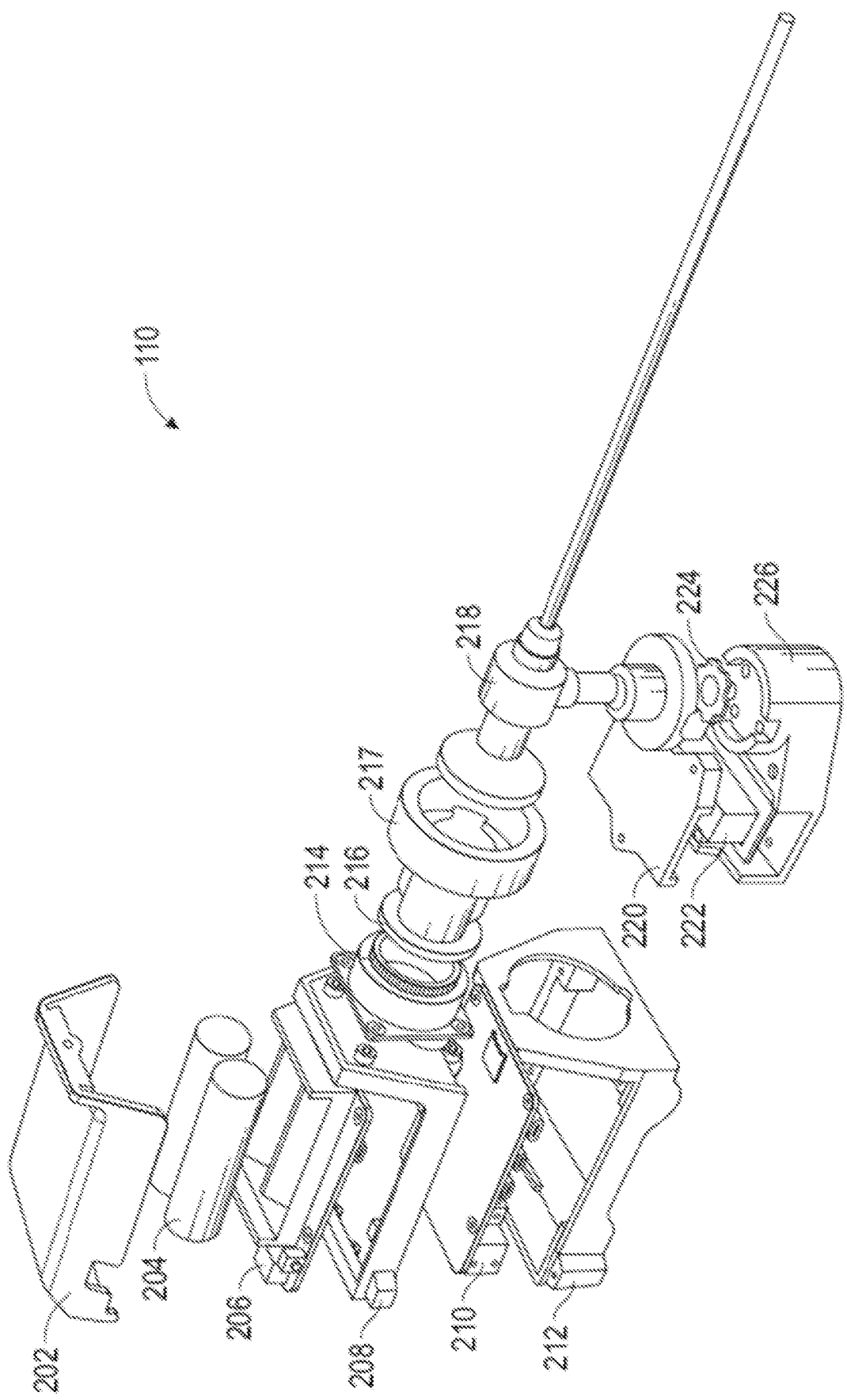

HANDHELD WIRELESS ENDOSCOPE IMAGE STREAMING APPARATUS

CROSS-REFERENCE TO RELATED APPLICATIONS

This application is a non-provisional application and claims the benefit of provisional U.S. Patent Application No. 63/225,440, filed Jul. 23, 2021, which is hereby incorporated by reference in its entirety.

FIELD

This application related generally to endoscope devices, and more particularly, to systems and methods for a handheld wireless endoscope image streaming apparatus.

BACKGROUND

Traditional endoscopic systems are prohibitively bulky and difficult to use. In typical wired endoscopic devices, the endoscopic device is connected to a computer system by one or more cables that may transmit imagery, light, and power. However, the cables are bulky, hard to sanitize, and weigh the instrument down. Moreover, they render the device difficult to maneuver and to transport. In existing wireless endoscopic systems, the endoscopic device requires a dedicated receiver box for communicating with the endoscopic device. These systems are expensive, take up more physical space, and are difficult to transport. It would be desirable for an endoscopic device to stream imagery wirelessly to a computer system without requiring an external receiver box to avoid the disadvantages of traditional systems.

SUMMARY

In general, one innovative aspect of the subject described in this specification can be embodied in systems, computer readable media, and methods for a handheld wireless endoscopic image streaming apparatus. One system comprises a portable wireless endoscope system comprising a hand-held body comprising a housing, the housing containing a battery-operated onboard processor, a wireless transceiver, a digital camera and a storage system contained within the housing, and the housing having an endoscope coupler with a lens and an attachment connector. The system establishes a wireless connection to a computer system. The system obtains, via the digital camera, video imagery via an endoscope optically connected to the endoscope coupler, the video imagery including multiple frames. The system analyzes each of the multiple frames of the obtained video imagery and adjusts one or more characteristics of a frame. The system creates modified video data of the adjusted one or more frames. The system streams to the computer system, via the wireless transceiver, the modified video data.

In another aspect of the system, the system receives from the computer system, via the wireless transceiver, instructions to initiate a video streaming service on the endoscope system. Based on the received instructions, the system starts the video streaming service.

In another aspect of the system, the system receives a start command from the computer system to begin obtaining video imagery. Based on the received command, the system starts image acquisition by the camera of endoscope system. The system receives a stop command from the computer system to stop obtaining video imagery. Based on the received stop command, the system stops image acquisition by the camera.

In another aspect of the system, the system creates a video file having multiple frames of the modified video data. The system determines whether a frame of the video file includes any imagery outside of a patient's body. If the frame is determined to include imagery outside of a patient's body, then the system deletes the frame.

In another aspect of the system, the system controls a light source to illuminate an endoscope optically coupled to the wireless endoscope system.

In another aspect of the system, the system determines an average luminosity across multiple pixels of a frame. The system adjusts power being passed to the light source to increase or decrease the luminosity of the light source to a predetermined luminosity value or range.

In another aspect of the system, the system establishes a connection with the computer system, where the computer system has determined the IP address of the endoscope system.

In another aspect of the system, the system initiates a video streaming receiver service on the computer system.

In another aspect of the system, the system determines whether the endoscope system has required versions of software packages installed on the endoscope system. The system automatically updates or installs required versions of the software packages.

In another aspect of the system, the one or more characteristics of the frame include heat transfer and artificial illumination.

Further areas of applicability of the present disclosure will become apparent from the detailed description, the claims and the drawings. The detailed description and specific examples are intended for illustration only and are not intended to limit the scope of the disclosure.

BRIEF DESCRIPTION OF THE DRAWINGS

The present disclosure will become better understood from the detailed description and the drawings, wherein:

FIG. 2A illustrates an exploded view of an embodiment of an endoscopic device.

DETAILED DESCRIPTION

Figure 1:
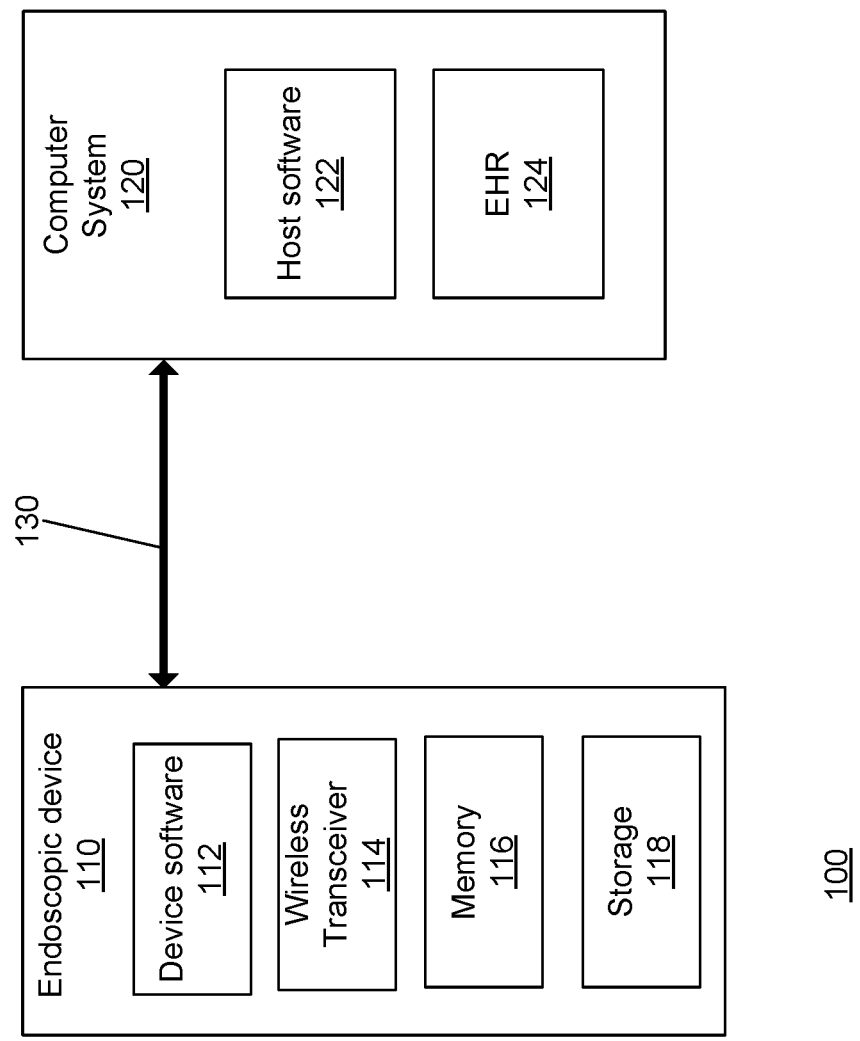
FIG. 1 illustrates an exemplary environment where embodiments of a handheld wireless endoscopic image streaming apparatus may operate.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

In addition, it should be understood that steps of the exemplary methods set forth in this exemplary patent can be performed in different orders than the order presented in this specification. Furthermore, some steps of the exemplary methods may be performed in parallel rather than being performed sequentially. Also, the steps of the exemplary methods may be performed in a network environment in which some steps are performed by different computers in the networked environment.

Some embodiments are implemented by a computer system. A computer system may include a processor, a memory, and a non-transitory computer-readable medium. The memory and non-transitory medium may store instructions for performing methods and steps described herein.

FIG. 1 illustrates an exemplary environment 100 where embodiments of a handheld wireless endoscopic image streaming apparatus may operate. Endoscopic device 110 may comprise a handheld wireless apparatus for streaming endoscopic images. Endoscopic device 110 may capture, for example, endoscopic video and photos. Endoscopic device 110 may include device software 112 stored and operating on the device. Computer system 120 may comprise a computer system such as desktop, laptop, tablet, server, mobile device, embedded device, augmented reality/virtual reality device, and other computer systems. The endoscopic device 110 and computer system 120 may be wirelessly connected via connection 130. Connection 130 may comprise a network, such as a local wireless network, intranet, local area network, the Internet, or other network. Computer system 120 may include host software 122 that interfaces and communicates over connection 130 with device software 112 and may include electronic health records (EHR) system 124. The EHR 124 may comprise a digital version of patient medical charts that are maintained by a medical provider for a plurality of patients. In some embodiments, the EHR 124 may be stored on an external server and accessed by the computer system 120 through a network.

In exemplary environment 100, endoscopic device 110 wirelessly streams endoscopic imagery directly to computer system 120 without needing an intermediate device such as a receiver box or cable box to communicate with computer system 120, which favorably impacts the cost of the system, reduces space needs, and improves portability. In one embodiment, the endoscopic device 110 may be portable between different computer systems in different clinical areas, allowing the endoscopic device 110 to be transported with little or no external equipment.

FIG. 2A illustrates an exploded view of an embodiment of the endoscopic device 110. Endoscopic device 110 may comprise a case, including a top case portion 202, middle case portion 208, and bottom case portion 212. The case may be made of any material such as plastic, metal, composites, and other materials. In some embodiments, the case may comprise a 3D printed plastic enclosure. The case may be ergonomic and easy to hold. In some embodiments, the endoscopic device 110 may be configured to fit in one hand. Endoscopic device 110 may include or more batteries 204 for powering the device. Batteries 204 may rest in the battery board 206 for holding the batteries and electrically connecting the batteries 204 to the other components of the device. In some embodiments, the batteries 204 may be rechargeable, such as via a power cable or wireless charging system of endoscopic device 110 or in a separate charging system. Processor 210 may store and execute instructions to perform operations described herein. Processor 210 may be connected to memory and a storage system comprising permanent storage for storing instructions and data. Processor may be connected to a wireless transceiver for transmitting and receiving data over wireless connection 130. In some embodiments, referring to FIG. 1, the processor 210, memory 116, storage system 118, and wireless transceiver 114 may be embedded on one or more circuit boards.

Digital camera 214 may be controlled by processor 210 and be configured for capturing video and still images. Endoscope coupler may comprise a lens 216 and attachment connector 217. Lens 216 may be used in conjunction with digital camera 214 to focus light on the digital sensor of the digital camera 214. Attachment connector 217 may comprise a mechanical attachment for coupling an endoscope 218. Endoscope 218 may comprise a flexible tube for inserting into the cavity of the body of a patient to capture medical images. The endoscope 218 may attach and detach from attachment connector 217. Attachment connector 217 may be configured to couple with a variety of different types and models of endoscopes.

Light case may comprise a top light case portion 220 and bottom light case portion 226 for housing light 224. Light 224 may comprise a light source, such as a light-emitting diode (LED), for radiating light into the endoscope 218 to enable the digital camera 214 to capture imagery. Boost converter 222 may be housed in the light case and may adjust voltage and current from the device to be suitable to power the light 224. In one embodiment, the light 224, light case, and boost converter 222 are attachable and detachable to the side of the endoscope 218.

Figure 2B:
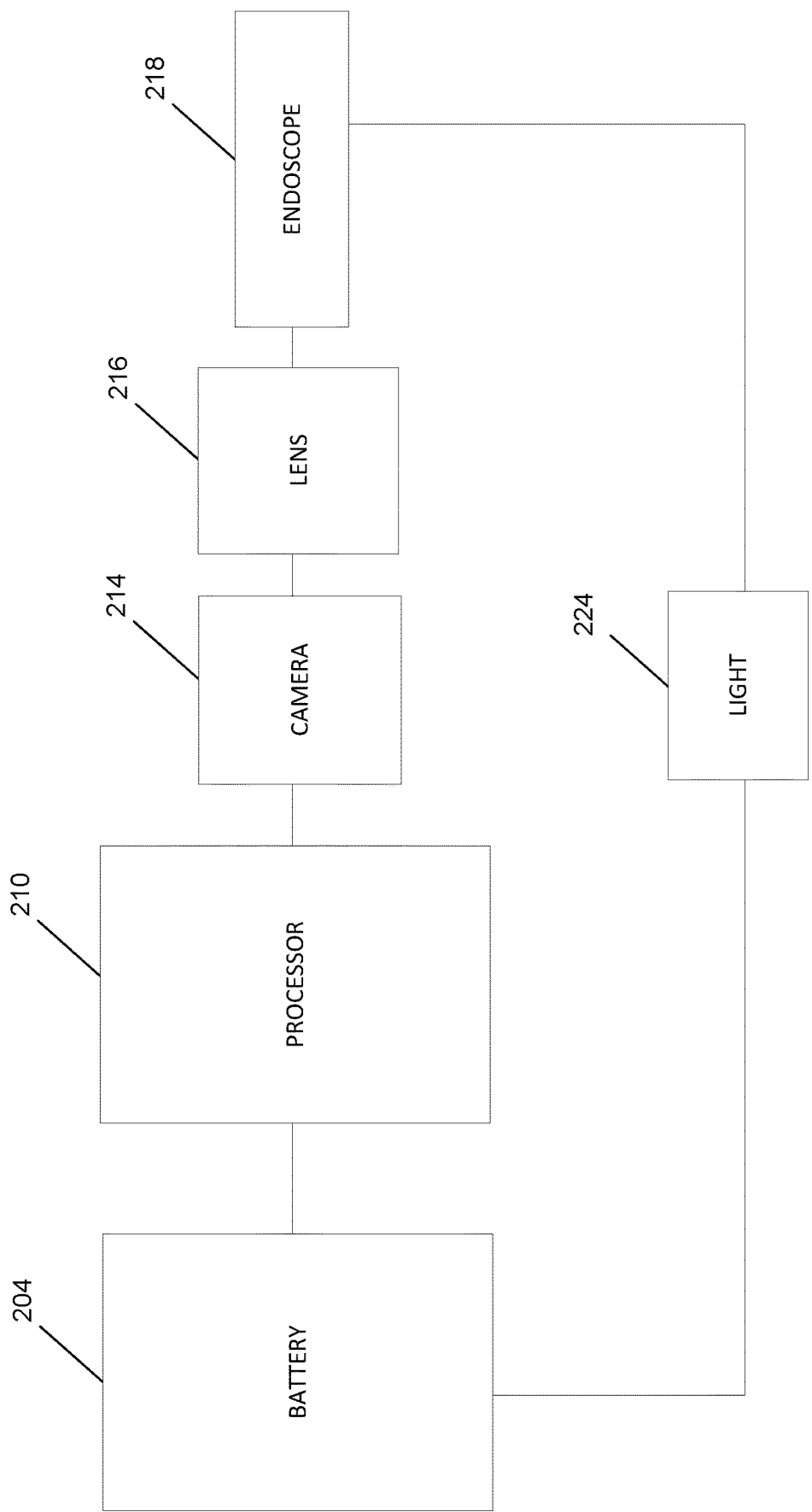
FIG. 2B illustrates an exemplary block diagram of an embodiment of an endoscopic device.

FIG. 2B illustrates an exemplary block diagram of an embodiment of the endoscopic device 110. Battery 204 may be electrically connected to processor 210 to provide a power source. Processor 210 may be connected to camera 214 and control its operation with electrical signals. Camera 214 may be optically coupled to lens 216, which is optically connected to endoscope 218 through which imagery passes and is captured.

In an embodiment, light 224 is powered by battery 204. Power from the battery 204 may run through an operational amplifier voltage follower circuit, which may use a digital to analog converter of the processor 210 as a reference voltage. Then power may run through boost converter 222 to increase the voltage and reduce current of the electrical circuit to a suitable range for light 224. In some embodiments, the light 224 may require a higher voltage than used by the processor 210 or that is provided by the battery 204 without boost converter 222. The output voltage of the boost converter 222 may be adjustable to enable configuration of the device for different types of light 224. The light 224 may be optically connected to the endoscope 218 to radiate light into the endoscope from its proximal end to the distal end in the cavity of a patient's body.

Figure 3A:
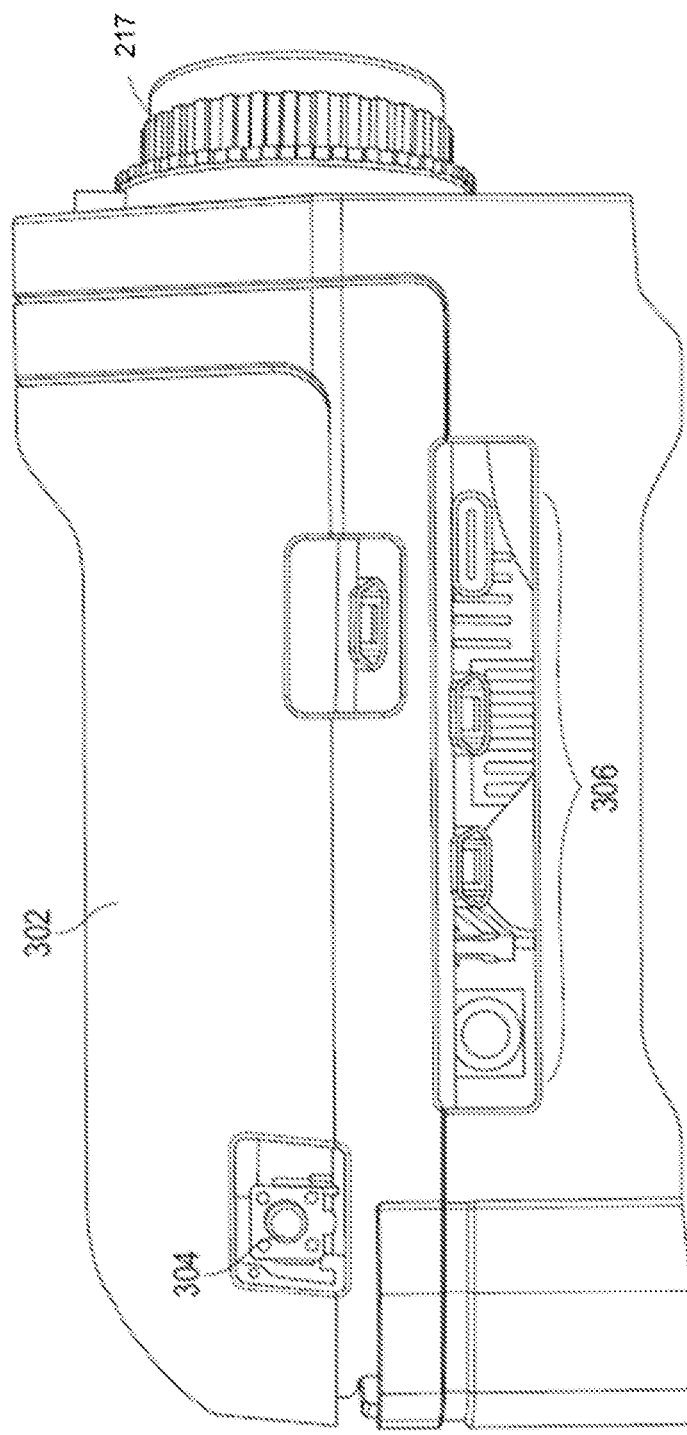
FIG. 3A illustrates a left side view of an embodiment of an endoscopic device.

FIG. 3A illustrates a left side view of an embodiment of the endoscopic device 110. Case 302 may comprise a housing for the components of the device. Endoscopic device 110 may include a power button 304 and one or more ports 306 for optionally connecting to a power cable and for wired transmission and receipt of data from a computer system 120. During normal endoscopic operation, the endoscopic device 110 may communicate wirelessly with computer system 120 without being plugged in. Ports 306 may be configured for use during special operations, connecting external adapters and components, debugging, recharging, and so on. Attachment connector 217 is shown with endoscope 218 detached.

Figure 3B:
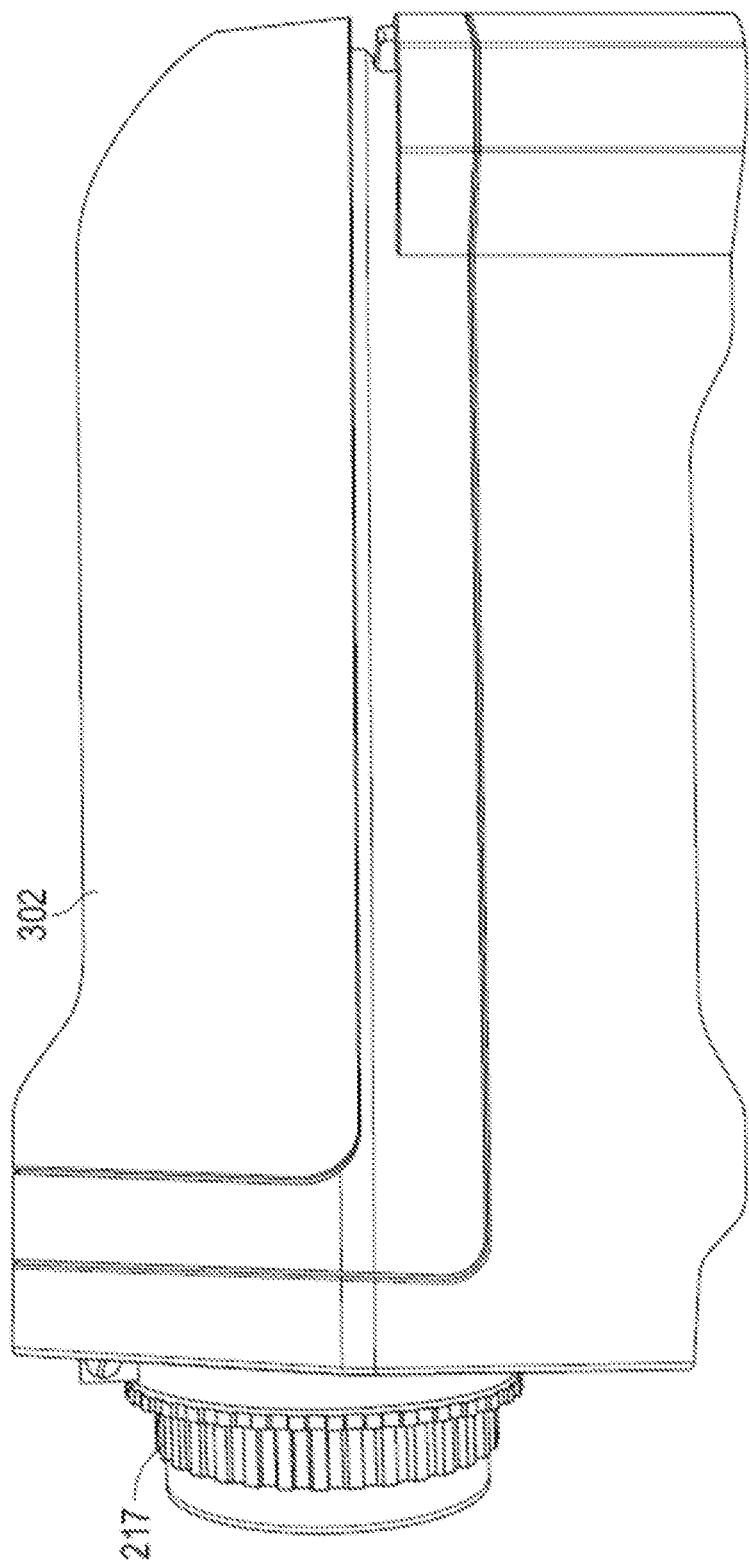
FIG. 3B illustrates a right side view of an embodiment of an endoscopic device.

FIG. 3B illustrates a right side view of an embodiment of the endoscopic device 110.

Figure 3C:
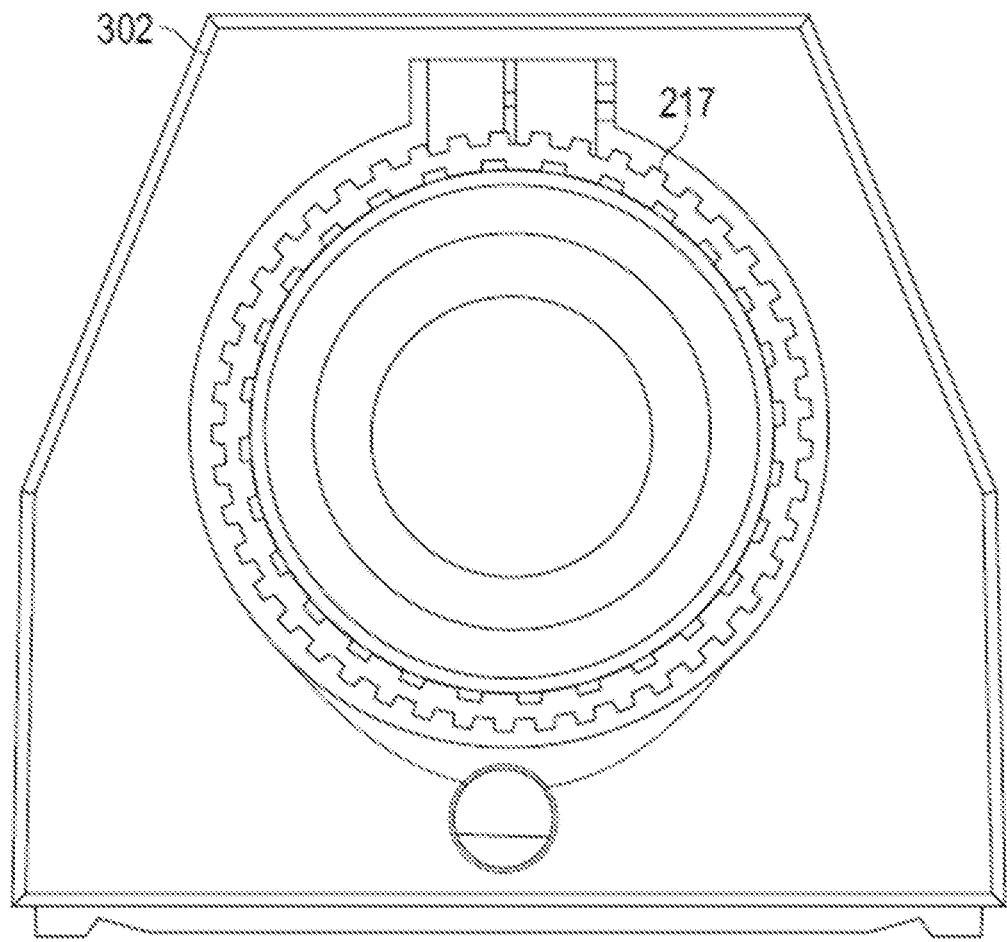
FIG. 3C illustrates a front view of an embodiment of an endoscopic device.

FIG. 3C illustrates a front view of an embodiment of the endoscopic device 110.

Figure 4:
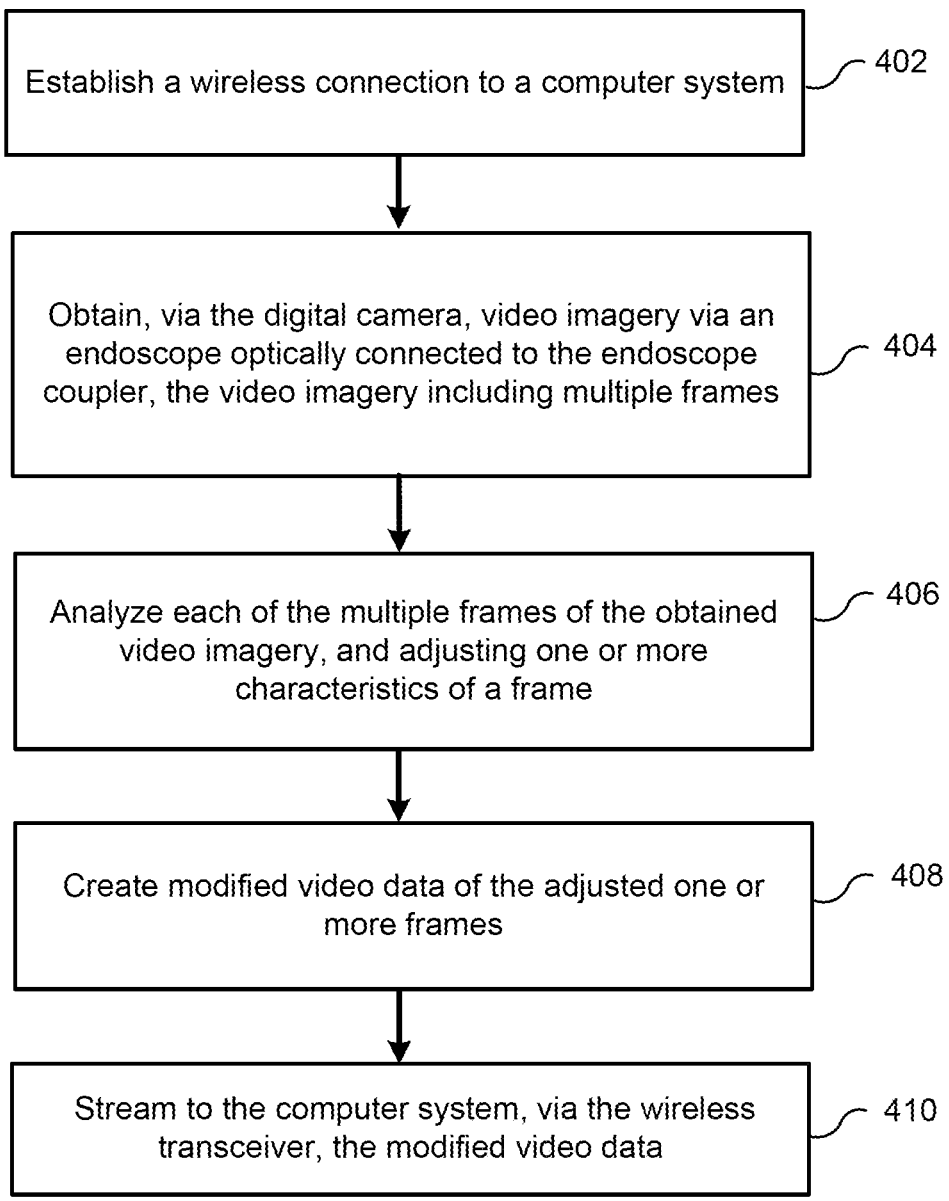
FIG. 4 illustrates an exemplary method 400 for wirelessly transmitting frames to a computer system.

FIG. 4 illustrates an exemplary method 400 for analyzing and adjusting one or more frames of video imagery by the endoscopic device 110 and wirelessly transmitting the frames to computer system 120. In step 402, endoscopic device 110 establishes a wireless connection to a computer system 120. The wireless connection may be established through a pairing process between the endoscopic device 110 and computer system 120 and may be configured to connect over a wireless protocol such as Wi-Fi (e.g., Wifi 802.11n/ac/ax), Bluetooth, or other protocols.

In step 404, the endoscopic device 110 obtains, via the digital camera 214, video imagery via an endoscope 218 optically connected to the endoscope coupler, the video imagery including multiple frames. Imagery from the distal end of the endoscope 218 in the patient's body may be optically transmitted through the endoscope 218 to the digital sensors of digital camera 214, such as by fiber optic cable. Endoscope 218 may be optically connected to light 224. Light may be optically transmitted from light 224 from the proximal end of the endoscope 218 through the length of the endoscope 218 to its distal end to illuminate the patient's body to allow capturing imagery.

In step 406, the endoscopic device 110 analyzes each of the multiple frames of the obtained video imagery and adjusts one or more characteristics of a frame. Processor 210 may perform image processing to adjust various characteristics of video frames such as image brightness, resolution, frame rate, contrast, color correction, visual enhancement, and so on. In some embodiments, processor 210 may perform additional processing such as artificial intelligence techniques for object detection for detecting medically significant portions of a frame, such as tumors or abnormalities. In some embodiments, one or more characteristics of a frame may further include heat transfer, artificial illumination, and other characteristics.

In step 408, the endoscopic device 110 creates modified video data of the adjusted one or more frames. The modified video data may incorporate the image processing and adjustments made by the processor 210 in step 406.

In step 410, the endoscopic device 110 streams to the computer system 120, via the wireless transceiver, the modified video data. The modified video data may be streamed in real-time to enable a clinician to view the modified video data on the computer system 120 in real-time while manipulating the endoscope 218 in the patient's body.

Figure 5:
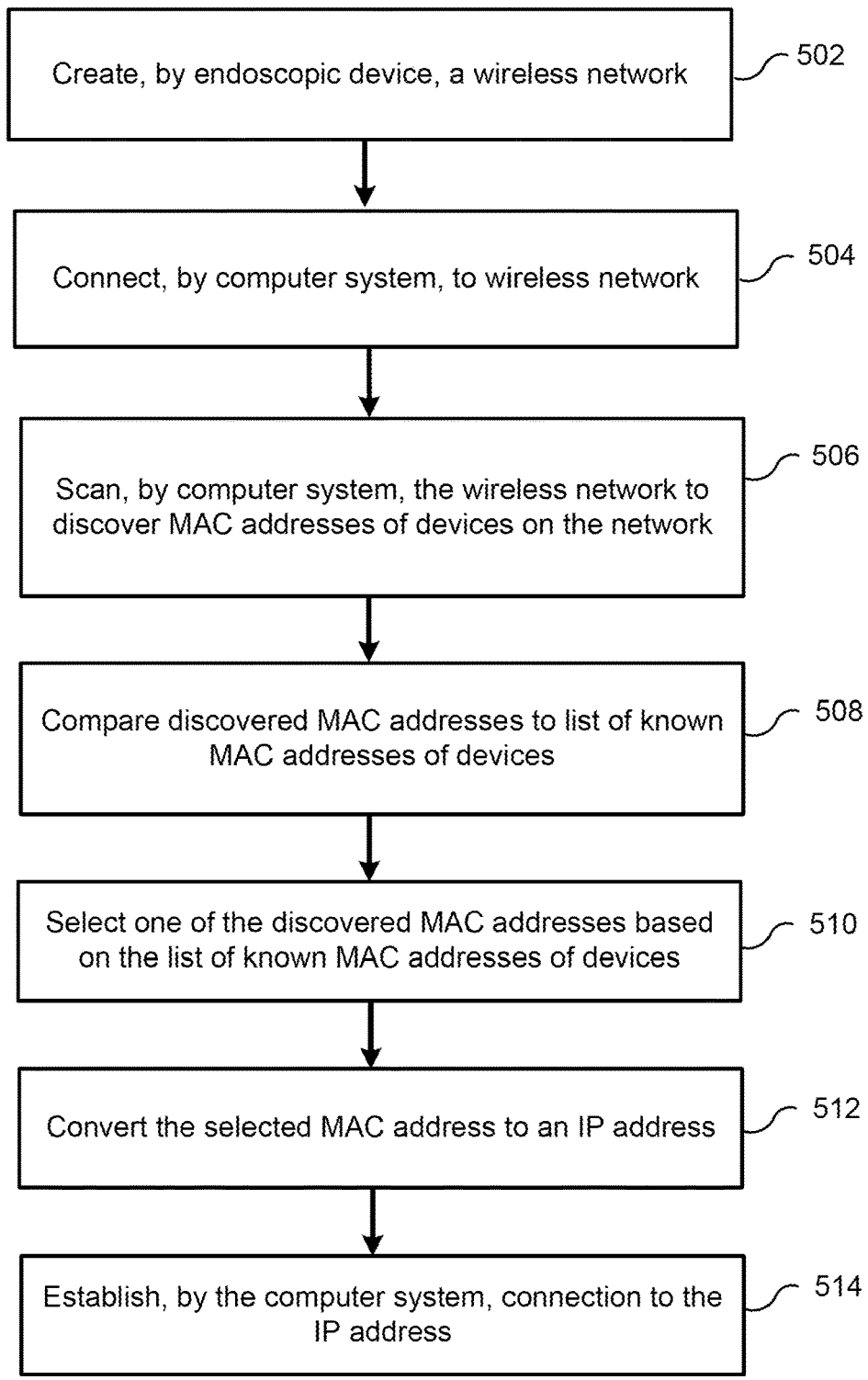
FIG. 5 illustrates an exemplary method for establishing a wireless connection between an endoscopic device and a computer system.

FIG. 5 illustrates an exemplary method 500 for establishing a wireless connection between the endoscopic device 110 and computer system 120. Method 500 may comprise an exemplary method of pairing the endoscopic device 110 and computer system 120 to enable streaming imagery from the endoscopic device 110 to the computer system 120 and may comprise an embodiment of step 402.

In step 502, the endoscopic device 110 creates a wireless network, such as a Wi-Fi, Bluetooth, or other wireless network. The wireless network may be established by the wireless transceiver in accordance with instructions from the processor 210. In an embodiment, the endoscopic device 110 creates the wireless network automatically when it is turned on via power button 304. In some embodiments, the wireless network has an identifier, which is optionally pre-configured, to identify it as belonging to endoscopic device 110.

In step 504, the computer system 120 connects to the wireless network. The computer system 120 may include a wireless transceiver that monitors for wireless networks. The computer system 120 may scan for wireless networks and may connect to a wireless network comprising an identifier that is known to be associated with endoscopic device 110. In some embodiments, one or more known identifiers for the wireless network may be configured in host software 122.

In step 506, the computer system 120 scans the wireless network to discover Media Access Control (MAC) addresses of devices on the network. A MAC address may comprise a hardware address of a computer device, which in some embodiments may be hardcoded. Computer system 120 may scan the wireless network by pinging devices on the network or passively monitoring data packets on the network. Computer system 120 may discover the MAC address of each active device on the wireless network.

In step 508, the computer system 120 may compare discovered MAC addresses on the wireless network to a list of known MAC addresses of devices. The list of known MAC addresses of devices may comprise a list of MAC addresses of endoscopic devices, or a larger set of candidate devices that may be endoscopic devices. For example, in an embodiment, the list of known MAC addresses includes the addresses of processors or network adapters comprising components of endoscopic device 110, but which may also comprise components of other digital devices as well. The computer system 120 may determine whether discovered devices on the network comprise an endoscopic device based on comparing the discovered MAC addresses to the list of known MAC addresses of devices. In some embodiments, the list of known MAC addresses of devices may be generated during the manufacturing process for endoscopic devices 110 or processors 210.

In step 510, the computer system 120 may select one of the discovered MAC addresses based on the list of known MAC addresses of devices. When a match between a discovered MAC address and a MAC address on the list is found, then the computer system 120 may select the discovered MAC address. The computer system 120 may flag that the discovered MAC address is for an endoscopic device or may be a candidate for being an endoscopic device. When a discovered MAC address does not match an address on the list, then the computer system 120 may discard the MAC address as not relevant.

In step 512, the computer system 120 may convert the selected MAC address to an Internet Protocol (IP) address. An IP address may comprise a network address of a device that allows transmitting data to and receiving data from the device over a network. In some embodiments, the computer system 120 may look up the MAC address in an address table that contains pairs of associated MAC and IP addresses. Using the address table, the computer system 120 may convert a MAC address into an associated IP address on the wireless network. The computer system 120 may store the address table or may retrieve the address table from an external device.

In step 514, the computer system 120 may establish a connection to the IP address. The IP address being the network address of the endoscopic device 110, a connection between the endoscopic device 110 and computer system 120 is established. In some embodiments, the endoscopic device 110 and computer system 120 may perform a handshake to confirm that the IP address belongs to the endoscopic device 110 and that the endoscopic device 110 and computer system 120 are authenticated. In some embodiments, the connection is established using a protocol with sufficient bandwidth and low latency to enable receipt of video imagery. Optionally, the connection may be encrypted. In some embodiments, the connection comprises a Secure Shell Protocol (SSH) connection that enables the computer system 120 to execute commands on the endoscopic device 110 via remote access.

Additional variations of method 500 may be used in some embodiments. Alternatively, in steps 502 and 504, the computer system 120 may create a wireless network and endoscopic device 110 may connect to the wireless network. In a variation, in steps 502 and 504, the endoscopic device 110 and computer system 120 may both connect to an existing wireless network in the clinical location. Moreover, in an alternative approach to steps 506-512, a process may be performed wherein the endoscopic device 110 broadcasts a message on the wireless network including an identifier identifying itself as endoscopic device 110 and its MAC address and IP address. Computer system 120 may receive the message and authenticate the identifier, such as using public key cryptography or symmetric key cryptography, to confirm that the sender of the message is the endoscopic device 110. Computer system 120 may establish a connection to the IP address.

Vice versa, in an alternative approach to steps 506-512, a process may be performed wherein the computer device 120 broadcasts a message on the wireless network including an identifier indicating a request to connect to an endoscopic device and its MAC address and IP address. Endoscopic device 110 may receive the message and authenticate the identifier, such as using public key cryptography or symmetric key cryptography, to confirm that the sender of the message is computer system 120. Endoscopic device 110 may transmit a message to the computer system 120 including an identifier identifying itself as endoscopic device 110 and its MAC address and IP address. Computer system 120 may establish a connection to the IP address.

Figure 6:
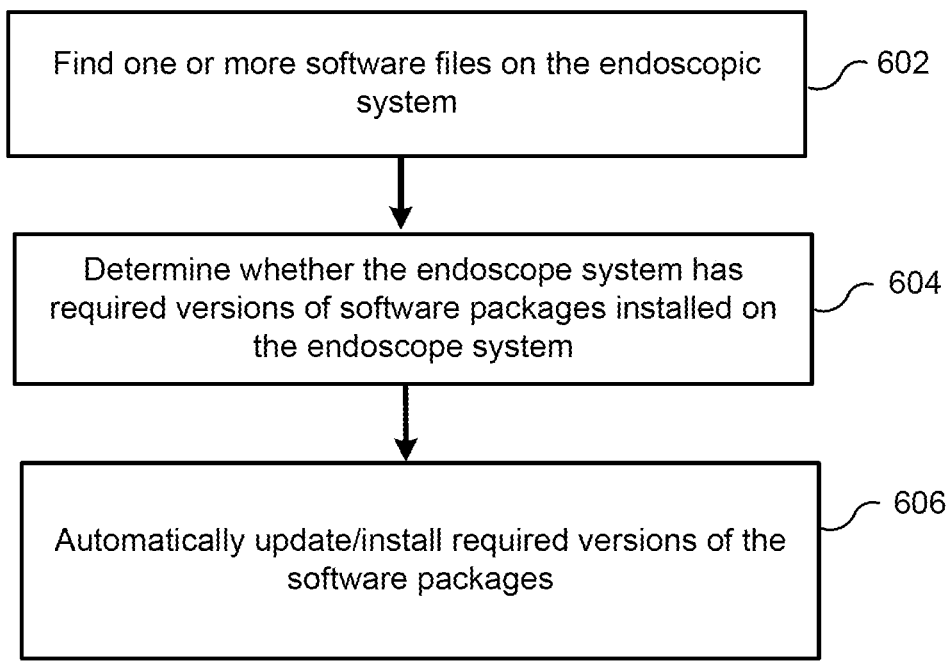
FIG. 6 illustrates an exemplary method for updating and installing software on an endoscopic device.

FIG. 6 illustrates an exemplary method 600 for updating and installing software on the endoscopic device 110. In an embodiment, after endoscopic device 110 and computer system 120 establish a wireless connection in step 402, the computer system 120 analyzes the device software 112 on the endoscopic device 110 to determine whether the device software 112 is out of date and, if so, updates and installs new software. The check for software updates may be initiated automatically after the pairing process to enable the endoscopic device 110 to immediately update its software when necessary, prior to sending imagery to the computer system 120.

In step 602, the computer system 120 finds one or more software files on the endoscopic device 110. The computer system 120 may access the file system on the storage system of the endoscopic device 110 via wireless connection 130 to search for and find software files of the endoscopic device 110. The software files may execute methods and processes herein such as methods 400, 500, 600, 700, 800, 900, 1000, 1100. In some embodiments, the computer system 120 may find the software files by opening and retrieving a file directory location where the software files are known to be located. The file directory location may be a pre-configured location, or the file directory location may be manually input to the computer system 120 during or before the update process. Alternatively, the computer system 120 may find the software files by searching the file system of the endoscopic device 110 for file names of the software files, where the file names may be pre-configured or manually input.

In step 604, the computer system 120 determines whether the endoscopic device 110 has required versions of software packages installed on the endoscopic device 110. The software packages may, for example, comprise software files. The computer system 120 may check the version of the software packages and compare with a list of latest version numbers of the software packages in host software 122. The host software 122 may update its list of latest version numbers of the software packages through a network, such as the Internet. In some embodiments, the software packages on the endoscopic device 110 may comprise version tags or fields storing their version number. In some embodiments, the computer system 120 may detect whether any expected software files on the endoscopic device 110 are missing by comparing the software files found on the endoscopic device 110 to the contents of a software repository. If the version numbers of the software packages on the endoscopic device 110 matches the latest software package version numbers identified in the host software 122 of computer system 120, then the software packages are not updated.

In step 606, the computer system 120 automatically updates/installs required versions of the software packages. If any of the software packages on the endoscopic device 110 comprise a version number that is less than the latest version number, or if any software packages are missing, then the computer system 120 updates the software package by transmitting the latest version of the software package from the computer system 120 to the endoscopic device 110 and installing it on the endoscopic device 110. The prior version of the software package on the endoscopic device may be replaced in the process. In some embodiments, the computer system 120 transfers the new version of the software package to the endoscopic device 110 using Secure File Transfer Protocol (SFTP) or other protocols. Optionally, the file transfer is performed via an encrypted connection.

Figure 7:
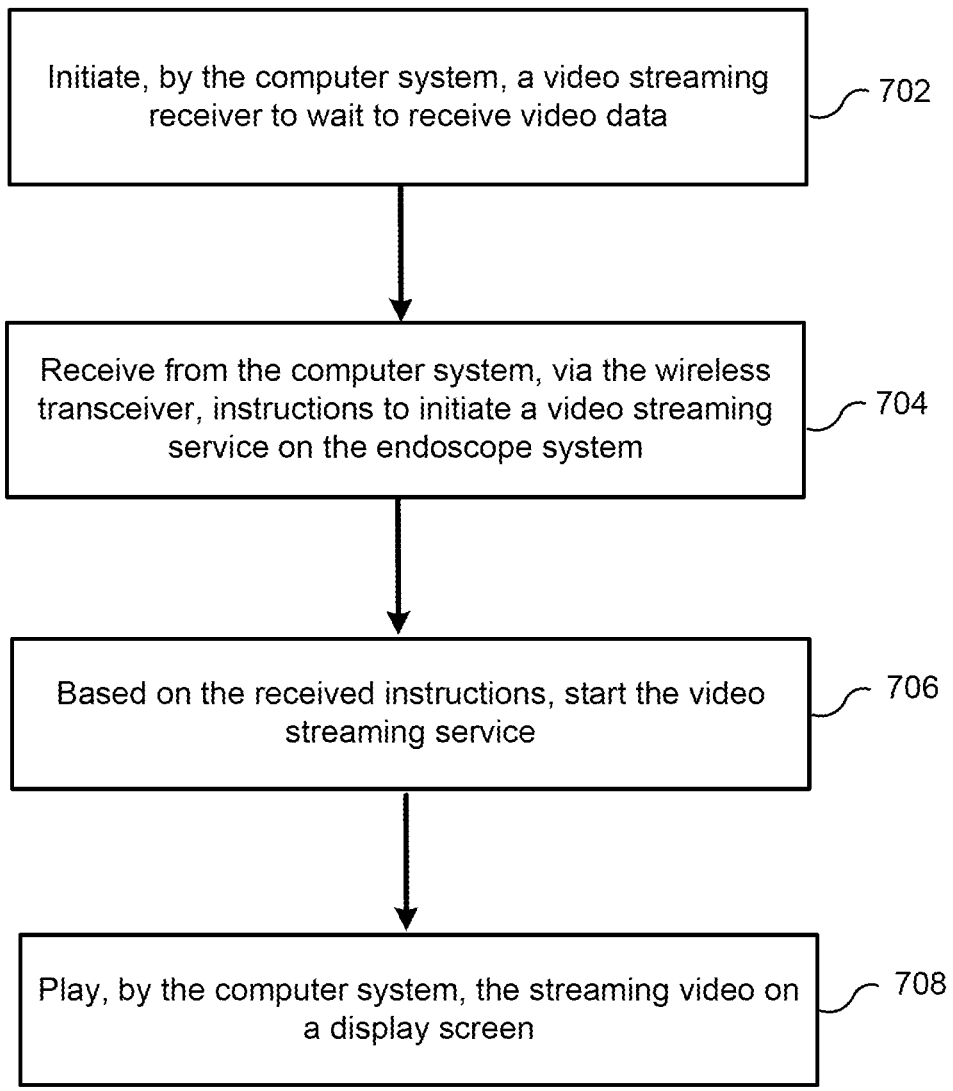
FIG. 7 illustrates an exemplary method for streaming video from an endoscopic device to a computer system.

FIG. 7 illustrates an exemplary method 700 for streaming video from the endoscopic device 110 to the computer system 120. In an embodiment, after the software package versions on the endoscopic device 110 are checked and updated, the process of streaming video may be initiated automatically.

In step 702, the computer system 120 may initiate a video streaming receiver service in the host software 122 to receive streaming video data from the endoscopic device 110. The video streaming receiver service waits to receive transmitted video data. The computer system 120 may transmit one or more instructions to the endoscopic device over the wireless connection 130 to begin streaming video.

In step 704, the endoscopic device 110 receives from the computer system 120, via the wireless transceiver, instructions to initiate a video streaming service on the endoscopic device 110.

In step 706, based on the received instructions, the endoscopic device 110 starts the video streaming service. A plurality of frames of video data are captured from the digital camera 214, optionally modified by the processor 210, and streamed from the endoscopic device 110 to the computer system 120.

In step 708, the computer system 120 receives the streamed plurality of frames of video data at the video streaming receiver service and plays the streaming video on a display screen in real-time.

In some embodiments, start and stop commands may be issued from the computer system 120 to initiate and cease video streaming by the endoscopic device 110. In an embodiment, a user may press a button on the computer system 120 to start video streaming, and the computer system 120 may transmit over the wireless connection 130 a start command to the endoscopic device 110. User input to start video streaming may also comprise voice commands, gestures, touch inputs, or other controls, which may be detected and received by the computer system 120.

The endoscopic device 110 may receive the start command from the computer system 120 to begin obtaining video imagery. Based on the received command, the endoscopic device 110 may start image acquisition by the camera 214 of the endoscopic device 110. Imagery may be streamed via the method 700 or other methods herein.

When the endoscopic procedure is complete, a user may press a button on the computer system 120 to stop streaming or issue a voice command, gesture, touch inputs, or other controls to stop streaming. The computer system 120 may transmit over the wireless connection 130 a stop command to the endoscopic device 110.

The endoscopic device 110 may receive the stop command from the computer system 120 to stop obtaining video imagery. Based on the received stop command, the endoscopic device 110 may stop image acquisition by the camera 214. The endoscopic device 110 may stop the video streaming service, and computer system 120 may stop the video streaming receiver service. The endoscopic device 110 may finalize creation and storage of a video file of the video data via method 1100 or other methods herein.

Figure 8:
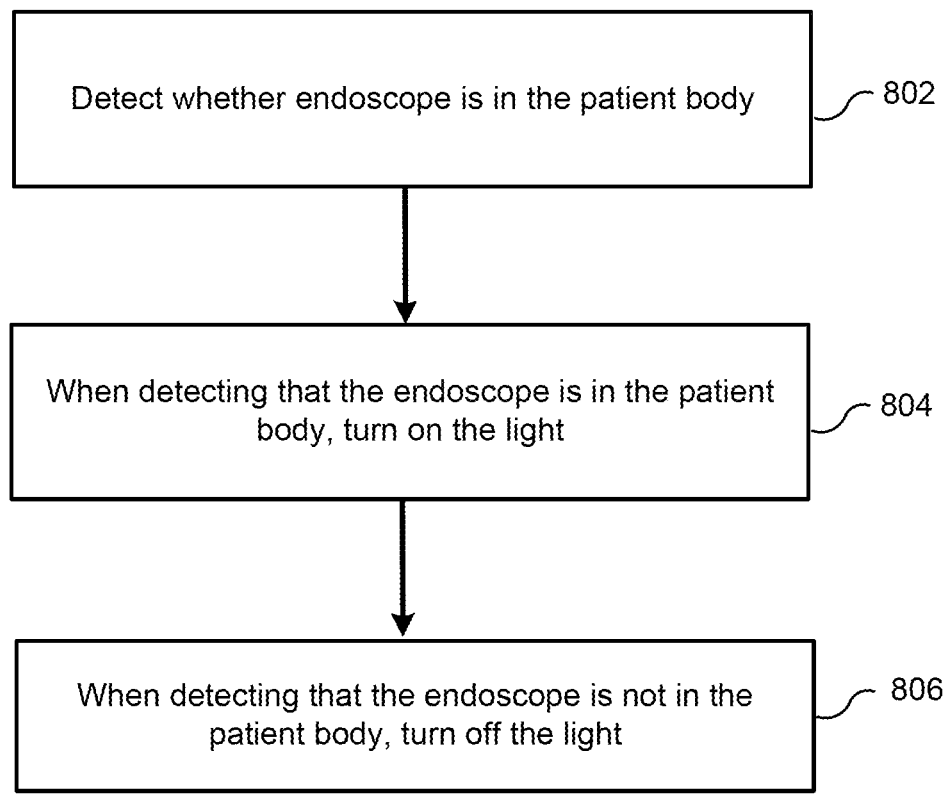
FIG. 8 illustrates an exemplary method for controlling a light based on whether an endoscope is in a cavity of a patient's body.

FIG. 8 illustrates an exemplary method 800 for controlling the light 224 based on whether the endoscope 218 is in the patient's body. In an embodiment, method 800 may be performed during the process of image capture and streaming by the endoscopic device 110, such as during steps 404, 406, 408, 706, and other steps herein.

In step 802, the endoscopic device 110 detects whether the endoscope 218 is in the patient's body cavity. In some embodiments, processor 210 analyzes one or more frames of video image data captured by camera 214 and performs image processing to determine whether the distal end of the endoscope 218 is in the patient's body cavity based on the frames.

In some embodiments, processor 210 analyzes the luminosity of the pixels of a frame to determine whether the pixels are dark or bright. When the pixels are dark, the endoscope 218 may be in a dark cavity such as the patient's body cavity. Processor 210 may compute the average luminosity of one or more pixels of a frame. When the average luminosity is below a pre-configured threshold brightness, then the processor 210 may determine that the endoscope 218 is in the patient's body cavity. In some embodiments, the processor 210 may monitor the change in luminosity of the pixels of video data between frames. When the processor 210 detects that the average luminosity of pixels of video data has become darker in later frames as compared to prior frames and the change in pixel luminosity exceeds a pre-configured threshold, then the processor may determine that the endoscope 218 is in the patient's body cavity.

In some embodiments, processor 210 analyzes the color of one or more pixels of a frame to determine whether the endoscope 218 is in the patient's body. The processor 210 may detect that the color distribution of one or more pixels of a frame matches the expected color distribution of an image taken in a patient's body and determine that the endoscope 218 is in the patient's body cavity. The processor 210 may analyze a color histogram of one or more pixels of a frame to determine the color distribution. In an embodiment, the processor 210 may detect that one or more portions of the frame comprise pixels that match one or more expected pixel colors of an image taken in a patient's body and determine that the endoscope 218 is in the patient's body cavity. In an embodiment, the processor 210 may detect that one or more portions of the frame comprise pixels that match one or more expected pixel colors of an image taken outside of a patient's body cavity and determine that the endoscope 218 is outside of the patient's body cavity. In an embodiment, the processor 210 may compute an average pixel color of one or more pixels of a frame and detect that the average pixel color matches one or more expected pixel colors of an image taken in a patient's body cavity and determine that the endoscope 218 is in the patient's body cavity.

In some embodiments, processor 210 uses a computer vision module to determine whether the endoscope 218 is in the patient's body cavity. The computer vision module may comprise an artificial intelligence (AI) program such as a neural network. In an embodiment, the computer vision module is trained on a plurality of labeled training images that are tagged as being inside the patient's body cavity or outside the patient's body cavity. The computer vision module may comprise one or more internal numerical parameters that are adjusted based on the training process to enable the computer vision module to classify unseen images as being inside the patient's body cavity or outside the patient's body cavity. The processor 210 may input a frame to the computer vision module and receive a classification output from the computer vision module that the frame is inside the patient's body cavity or outside the patient's body cavity. The processor 210 may determine the location of the endoscope 218 based on the classification output from the computer vision module.

In step 804, when the endoscopic device 110 detects that the endoscope 218 is in the patient's body, endoscopic device 110 turns on the light 224.

In step 806, when the endoscopic device 110 detects that the endoscope 218 is not in the patient's body, the device turns off the light 224. By turning off the light 224 when the endoscope 218 is not in the patient's body, the device may conserve battery power and also simplify operation of the device.

In some embodiments, the endoscope device 100 may automatically begin recording video when the device determines that the scope has been inserted into the body cavity. The endoscopic device 110 may automatically stop recording video when the device determines that the scope has been removed from the body cavity. Moreover, the endoscopic device 110 may evaluate recorded video and determine if any of the portions of the video depict imagery taken outside of the patient's body. In such instances, the endoscopic device 110 may delete those portions of record video.

In some embodiments, the endoscopic device 110 may record endoscopy video, de-identify patient sensitive data and upload the video to a separate computing device or server. For example, the system may use a trained machine learning network (such as a convolutional neural network) to identify and label pathology of images for significant findings (such as pathology, abnormal anatomy, etc.). The obtained videos may be catalogued and indexed with labels or other output of the trained machine learning network. A database of the videos may be searched and video imagery retrieved based on the key words as found in the database. Participating clinicians that use the endoscopic device 110 may access the video. This allows clinicians at different location to collaboratively review the endoscopy videos to assist in the care and treatment of patients.

Figure 9:
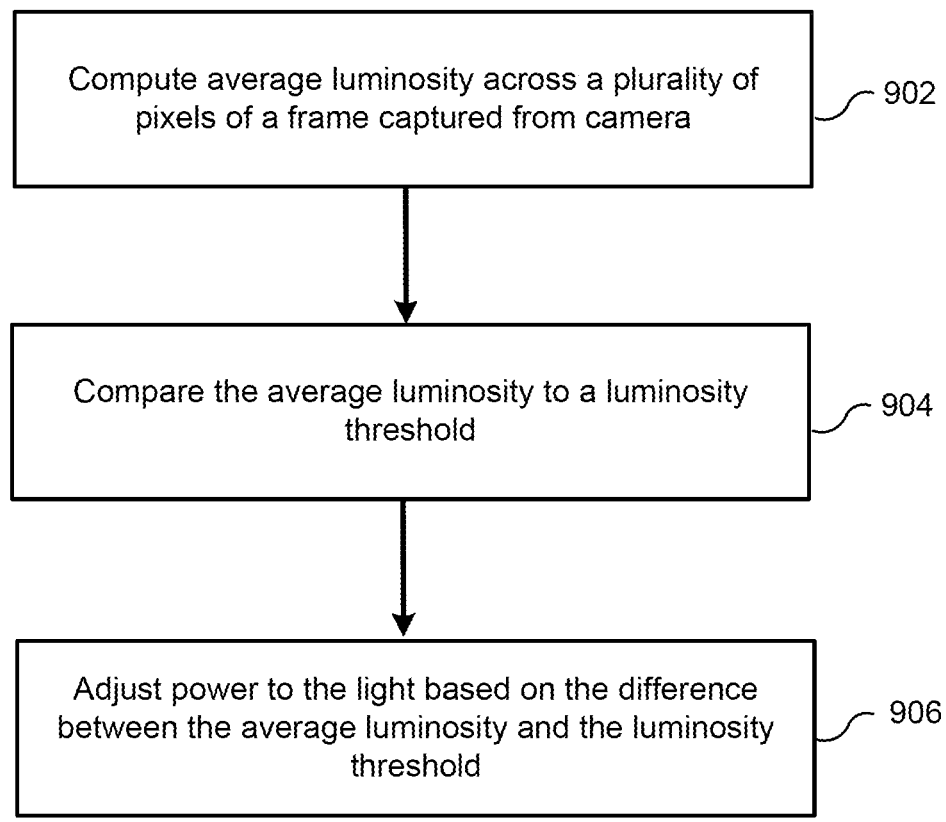
FIG. 9 illustrates an exemplary method for controlling power to a light.

FIG. 9 illustrates an exemplary method 900 for controlling power to the light 224. In an embodiment, method 900 may be performed during the process of video capture and streaming by the endoscopic device 110, such as during steps 404, 406, 408, 706, and other steps herein. Endoscopic device 110 may determine an average luminosity across multiple pixels of a frame and adjust power being passed to the light source to increase or decrease the luminosity of the light source to a predetermined luminosity value or range.

In step 902, processor 210 computes an average luminosity across a plurality of pixels of a frame captured from camera 214. The average luminosity may be computed over all or a subset of pixels of a frame.

In step 904, processor 210 compares the average luminosity to a luminosity threshold. The luminosity threshold may comprise a pre-configured threshold. In some embodiments, processor 210 may compare the average luminosity to a plurality of luminosity thresholds, such as an upper luminosity threshold and a lower luminosity threshold. In some embodiments, the luminosity threshold or thresholds may be configurable by a user.

In step 906, processor 210 adjusts power to the light based on the difference between the average luminosity and the luminosity threshold. In one embodiment, the processor 210 determines that the average luminosity is below the luminosity threshold (or below a lower luminosity threshold) and increases power to the light from battery 204 to increase the luminosity of the light. In one embodiment, the processor 210 determines that the average luminosity is above the luminosity threshold (or above an upper luminosity threshold) and decreases power to the light from battery 204 to decrease the luminosity of the light.

In some embodiments, the processor 210 may compute the amount of difference between the average luminosity and the luminosity threshold and compute an amount to adjust power to the light 224 based on the amount of difference. When the amount of difference is greater, the processor 210 may increase or decrease the power by a greater amount. When the amount of difference is lesser, the processor 210 may increase or decrease the power by a lesser amount. The processor 210 may calculate an amount to adjust power to the light 224 to increase or decrease the luminosity of the light to a predetermined luminosity value or range. In an embodiment, the predetermined luminosity value or range may be configurable by a user. The predetermined luminosity value or range may be dependent on a type of endoscopic procedure being performed with endoscopic device 110.

Figure 10:
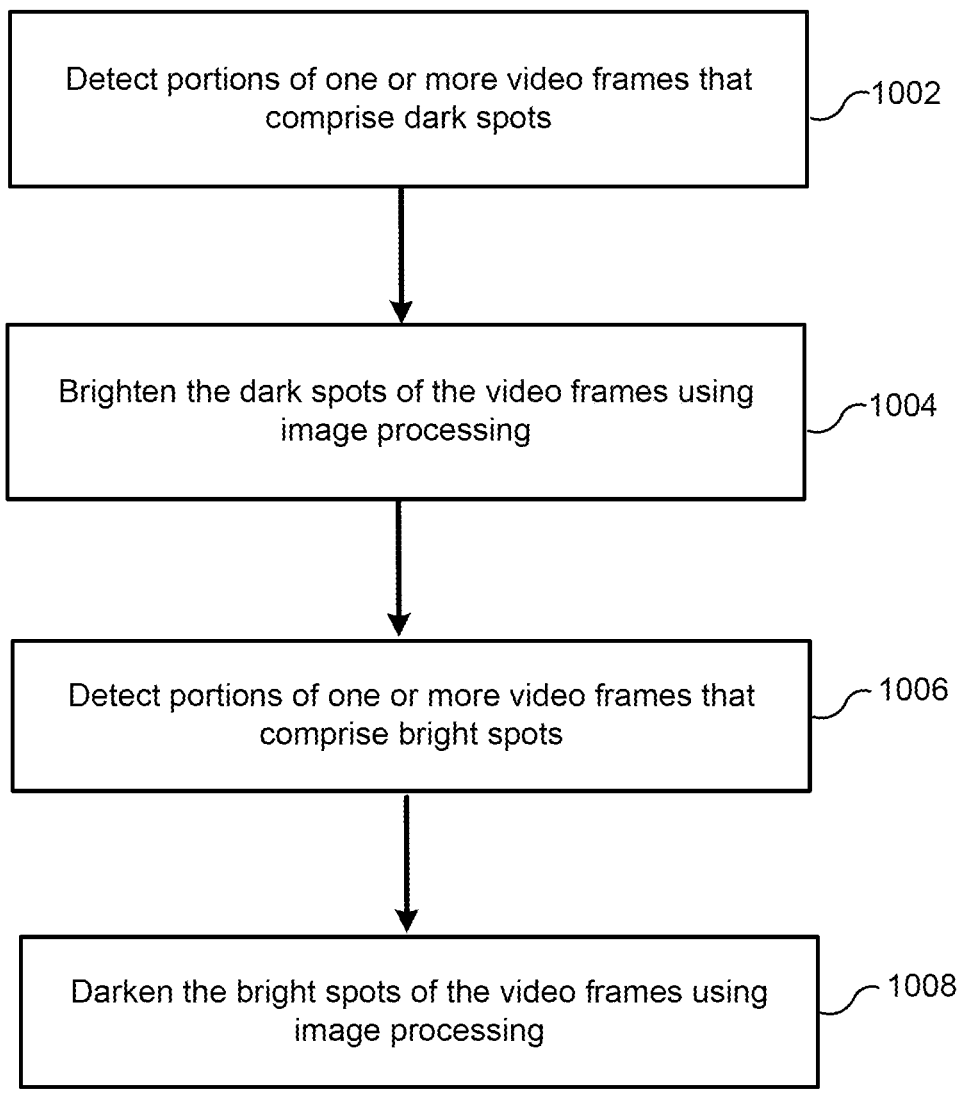
FIG. 10 illustrates an exemplary method for adjusting one or more frames of video to create modified video data.

FIG. 10 illustrates an exemplary method 1000 for adjusting one or more frames of video to create modified video data. In an embodiment, method 1000 may be performed during the process of video capture and streaming by the endoscopic device 110, such as during steps 404, 406, 408, 706, and other steps herein. Processor 210 may selectively adjust the luminosity of different portions of a frame to brighten dark spots and darken bright spots.

In step 1002, the endoscopic device 110 detects portions of one or more video frames that comprise dark spots. Processor 210 may detect one or more portions of a frame that have a lower than desired luminosity. In an embodiment, processor 210 may compute an average luminosity of one or more pixels comprising a portion of a frame and compare it to a luminosity threshold. Processor 210 may check that the light 224 is on and at a desired level of power or luminosity to determine that the light 224 does not require additional power. When it is determined that the light is on, the processor 210 may determine that the average luminosity of the pixels is below the luminosity threshold and that image processing should be applied. On the other hand, if the light 224 is off or at level of power or luminosity lower than a predetermined value or range, then the endoscopic device 110 may first turn on the light and adjust the power to the light using method 900 before repeating step 1002 and continuing in method 1000. In some embodiments, the luminosity threshold may comprise a preconfigured threshold and optionally the luminosity threshold may be configurable by a user.

In step 1004, the processor 210 may brighten the dark spots of the one or more video frames using image processing. The processor 210 may increase the luminosity of one or more pixels comprising the portion of the frame that is dark, such as by adjusting one or more pixel intensity values, until the pixels exceed the luminosity threshold.

In some embodiments, the processor 210 may increase the luminosity non-linearly across the one or more pixels of the dark portion of the frame. The processor 210 may increase the luminosity the greatest for pixels that are the darkest (having the greatest difference below the luminosity threshold) in the center of the dark portion and may increase the luminosity the least for pixels that are less dark (having the least difference below the luminosity threshold) at the edge of the dark portion. The increase in luminosity may peak in the center of the dark portion and gradually, non-linearly decline towards the edges of the dark portion.

In step 1006, the endoscopic device 110 detects portions of one or more video frames that comprise bright spots. Processor 210 may detect one or more portions of a frame that have a higher than desired luminosity. In an embodiment, processor 210 may compute an average luminosity of one or more pixels comprising a portion of a frame and compare it to a luminosity threshold. Processor 210 may check that the light 224 is on and at a desired level of power or luminosity to determine that the power and luminosity of the light 224 does not need to be decreased. The processor 210 may determine that the average luminosity is above a luminosity threshold and that image processing should be applied. On the other hand, if the light 224 has a level of power or luminosity greater than a predetermined value or range, then the endoscopic device 110 may first adjust the power to the light using method 900 before repeating step 1006 and continuing in method 1000. In some embodiments, the luminosity threshold may comprise a preconfigured threshold and optionally the luminosity threshold may be configurable by a user.

In step 1008, the processor 210 may darken the bright spots of the one or more video frames using image processing. The processor 210 may decrease the luminosity of one or more pixels comprising the portion of the frame that is bright, such as by adjusting the pixel values, until the pixels are below the luminosity threshold.

In some embodiments, the processor 210 may decrease the luminosity non-linearly across the one or more pixels of the bright portion of the frame. The processor 210 may decrease the luminosity the most for pixels that are the brightest (having the greatest difference above the luminosity threshold) in the center of the bright portion and may decrease the luminosity the least for pixels that are less bright (having the least difference above the luminosity threshold) at the edge of the bright portion. The decrease in luminosity may peak in the center of the bright portion and gradually, non-linearly decline towards the edges of the bright portion.

In some embodiments, the processor 210 may smooth changes in luminosity of a pixel between sequential frames of video to make changes in luminosity of the imagery appear more gradual. For example, when the processor 210 significantly adjusts the luminosity of a pixel in a first frame, it may optionally apply a limit to disallow completely removing the luminosity adjustment in the very next frame and instead spread the change in luminosity over several frames.

Method 1000 may be applied to a plurality of different portions of a frame to selectively brighten portions of the frame that are darker than a pre-configured threshold and to selectively darken portions of the frame that are brighter than a pre-configured threshold.

In some embodiments, a lower luminosity threshold may be used for dark spots in step 1002 and an upper luminosity threshold may be used for bright spots in step 1006, so that the modified video data is configured to represent a range of luminosity values. In some embodiments, the modified video data may include a tag to indicate that the video data is modified with adjusted luminosity.

Figure 11:
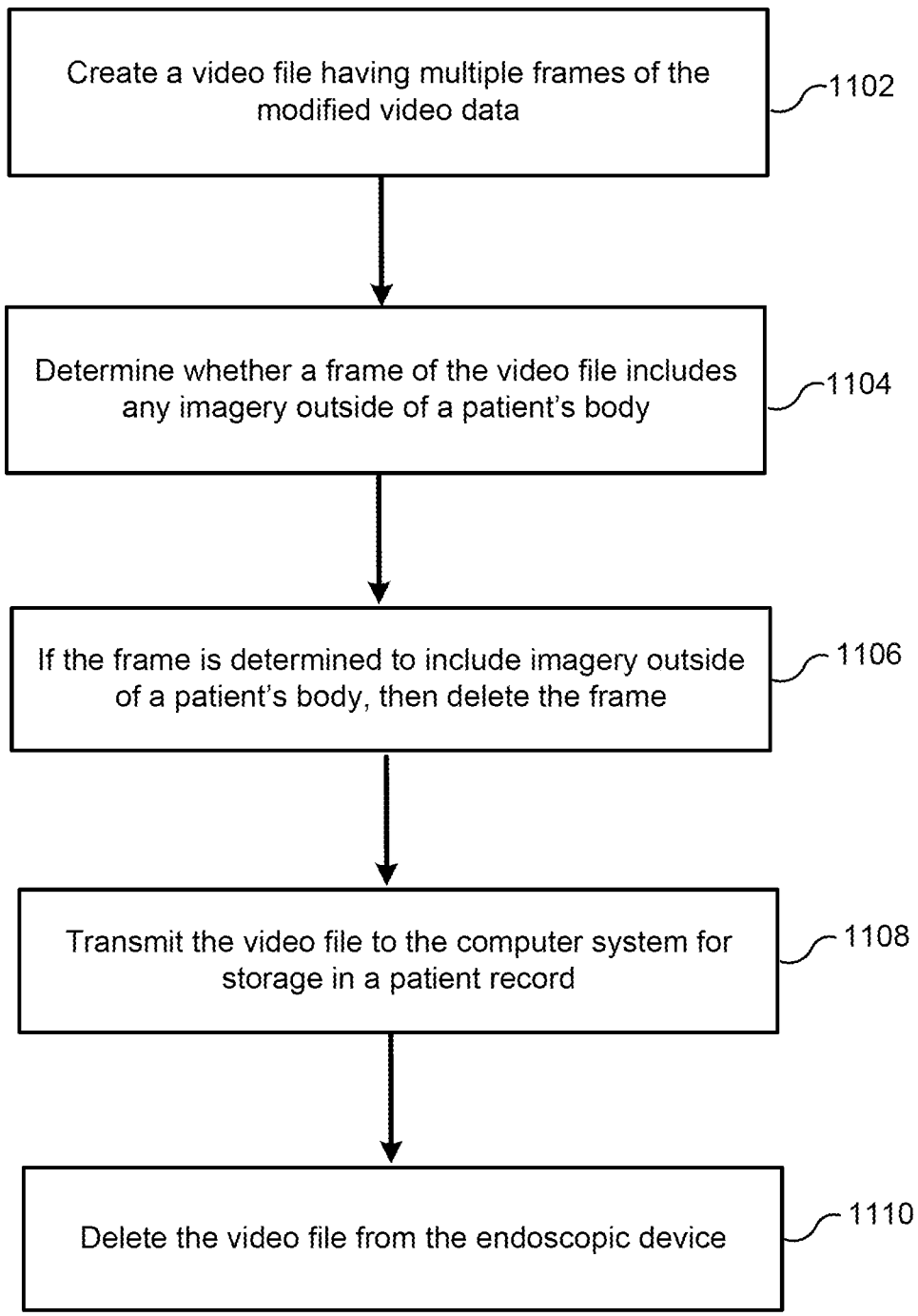
FIG. 11 illustrates an exemplary method for selectively deleting frames of a video file.

FIG. 11 illustrates an exemplary method 1100 for selectively deleting frames of a video file. In an embodiment, method 1100 may be performed after capture of video imagery is completed. For example, method 1100 may be performed after a stop command is received from the endoscopic device 110, and the device stops the video streaming service. Endoscopic device 110 may selectively delete frames of a video file to delete any personally identifiable information of the patient, or irrelevant information, in the video file.

In step 1102, the processor 210 creates a video file having multiple frames of the modified video data. In an embodiment, a stop command is received from the computer system 120, and the camera 214 stops acquiring image data and the processor 210 saves the video data it has captured (and optionally modified) into the video file.

In step 1104, the processor 210 determines whether a frame of the video file includes any imagery outside of a patient's body. In an embodiment, the processor 210 spawns a new process or thread to open the video file that was saved in step 1102 and analyze the frames of the video file. The processes described in step 802 and elsewhere herein for determining when a frame of video is inside or outside the patient's body may be used.

In some embodiments, the processor 210 may determine whether a frame includes any personally identifiable information through additional computer vision techniques. In an embodiment, the processor 210 may process the video frame with a face detector to detect any human faces in the frame. The face detector may comprise an artificial intelligence program, such as a neural network, and may scan the pixels of an image to determine if the pixels match characteristic features of a human face, such as eyes, nose, mouth, and other features. If a face is detected, then the frame may be determined to be outside the patient's body. In an embodiment, the processor 210 may apply text detection to the video frame to detect any text in the frame. The text detection may be performed by a text detector comprising an artificial intelligence program, such as a neural network. If text is detected, then the frame may be determined to be outside the patient's body.

In step 1106, if the frame is determined to include imagery outside of a patient's body, then the processor 210 may delete the frame. After deleting one or more frames of the video file, the processor 210 may save the edited video data in a new file on the storage system.

In step 1108, endoscopic device 110 may transmit the video file to the computer system 120 for storage in a patient record. In one embodiment, the endoscopic device 110 may upload the edited video file to EHR 124 using a Representational State Transfer Application Programming Interface (REST API). The edited video file may be stored in the patient's medical history.

In step 1110, endoscopic device 110 may delete the video file from the device. The processor 210 may delete the edited video file and modified video file from the storage system of the device. In an embodiment, the processor 210 actively writes garbage data over the edited video file and modified video file in the storage system to ensure they cannot be improperly retrieved. The processor 210 may optionally have an encrypted storage system such as an encrypted hard drive that stores the video files in an encrypted format. In one embodiment, the endoscopic device 110 waits for an acknowledgement message from the computer system 120 that the edited video file has been successfully saved in the patient record before deleting the video files from its storage system.

In some embodiments, the endoscopic device 110 may include sensors to determine the orientation or position of the endoscopic device in a 3-dimensional space. For example, the endoscopic device 110 may include a gyroscope and accelerometer to track the position and rotational movement of the endoscopic device. Maintaining proper orientation of the endoscopic device may be importation in certain use cases. For example, maintaining proper orientation would be important for a safe and accurate sinonasal endoscopy, especially in the context of a surgical procedure. In this example, an endoscopist or surgeon is responsible for maintaining proper orientation by assuring that the dorsal/superior aspect of the camera head unit is always parallel to the patient's midline and is point at the 12 o'clock position (or the patient's vertex). However, while in use, drifting or rotation of the endoscopic device 110 may occur, especially from hand-held use for an extended period of time. To account for this rotational drift, the endoscopic device 110 may perform an initialization procedure to set a position of the endoscopic device 110 in the 3-dimensional space. For example, the endoscopic device 110 may initialize it position to a "true north" orientation. At the beginning of an examination procedure, a camera of the endoscopic device 110 may be calibrated to a patient's anatomy. Although the anatomy of a patient does not vary, the patient's positions may vary from case to case (e.g., supine, recumbent, upright). The device may set its orientation position in response to an orientation command or an input such as physical button on the endoscopic device 110. A user interface may be provided, such as through a monitor or a hand-held computing device, where the user interface presents a grid with a representation of the endoscopic device. The user interface may be updated in real-time with the 3-dimensional orientation of the device (e.g., displaying the devices position relative to a x-, y-, z-axis).

In some embodiments, the endoscopic device 110 may initialize a 3-dimensional (3D) position of the hand-held body (or other components of the endoscopic device 110). The endoscopic device 110 may monitor the rotation of the hand-held body in at least an x-axis, y-axis and a z-axis. Where the rotation of the hand-held body rotates greater than a predetermined threshold angular value (i.e., an acceptable rotational value), the endoscopic device 110 may provide an alert to the operator of the device. For example, the endoscopic device 110 may monitor the degree of rotation of the endoscopic device 110 in any of the three degrees of rotation, and determine whether the endoscopic device rotates to a threshold predetermined value of acceptable rotation from the initialized position. The device may generate an alert (such as a haptic alert or audible alert) if the endoscopic device 110 has rotated to or past the threshold predetermined value. In some embodiments, a user interface may prompt the user of the endoscopic device 110 to rotate the device 110 in a direction to move the device's position back to or towards the initialized oriented position. In some embodiments, a vibration may be produced by the endoscopic device 110 to alert the device operator of the determined angular drift of the endoscopic device 110.

In some embodiments, a user interface may be displayed that depicts overlayed visualization of imagery obtained during an endoscopy procedure. The user interface may display an automatically scaled measurement grid and may display labels identifying key structures of the body cavity (e.g., the nasal septum, inferior turbinate, middle turbinate, choana, etc.).

Figure 12:
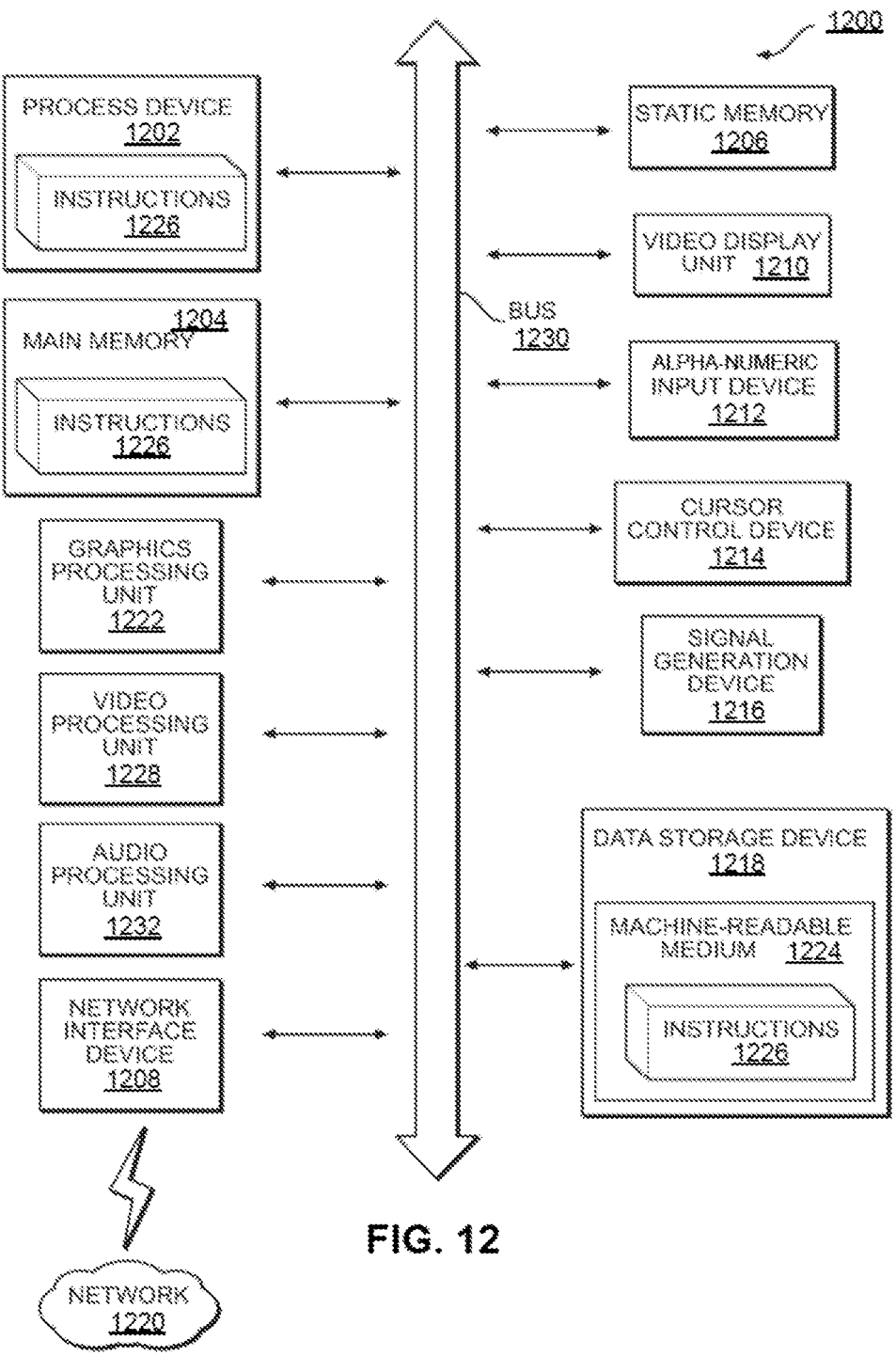
FIG. 12 illustrates an exemplary computer system for performing any one or more of the methodologies discussed herein.

FIG. 12 illustrates an example machine of a computer system within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 1200 includes a processing device 1202, a main memory 1204 (e.g., read-only memory (ROM), flash memory, dynamic random access memory (DRAM) such as synchronous DRAM (SDRAM) or Rambus DRAM (RDRAM), etc.), a static memory 1206 (e.g., flash memory, static random access memory (SRAM), etc.), and a data storage device 1218, which communicate with each other via a bus 1230.

Processing device 1202 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 1202 may also be one or more special-purpose processing devices such as an application specific integrated circuit (ASIC), a field programmable gate array (FPGA), a digital signal processor (DSP), network processor, or the like. The processing device 1202 is configured to execute instructions 1226 for performing the operations and steps discussed herein.

The computer system 1200 may further include a network interface device 1208 to communicate over the network 1220. The computer system 1200 also may include a video display unit 1210 (e.g., a liquid crystal display (LCD) or a cathode ray tube (CRT)), an alphanumeric input device 1212 (e.g., a keyboard), a cursor control device 1214 (e.g., a mouse) or an input touch device, a graphics processing unit 1222, a signal generation device 1216 (e.g., a speaker), graphics processing unit 1222, video processing unit 1228, and audio processing unit 1232.

The data storage device 1218 may include a machine-readable storage medium 1224 (also known as a computer-readable medium) on which is stored one or more sets of instructions or software 1226 embodying any one or more of the methodologies or functions described herein. The instructions 1226 may also reside, completely or at least partially, within the main memory 1204 and/or within the processing device 1202 during execution thereof by the computer system 1200, the main memory 1204 and the processing device 1202 also constituting machine-readable storage media.

In one implementation, the instructions 1226 include instructions to implement functionality corresponding to the components of a device to perform the disclosure herein. While the machine-readable storage medium 1224 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

In general, the terms "engine" and "module", as used herein, refer to logic embodied in hardware or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on one or more computer readable media, such as compact discs, digital video discs, flash drives, or any other tangible media. Such software code may be stored, partially or fully, on a memory device of the executing computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

Various general purpose systems may be used with programs in accordance with the teachings herein, or it may prove convenient to construct a more specialized apparatus to perform the method. The structure for a variety of these systems will appear as set forth in the description above. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. A portable wireless endoscope system, comprising:
a hand-held body comprising a housing, the housing containing a battery-operated onboard processor, a wireless transceiver, a digital camera and a storage system contained within the housing, and the housing having an endoscope coupler with a lens and an attachment connector, wherein the onboard processor is configured to perform the operations comprising:
creating, by the wireless endoscope system, a wireless network for connection by a computer system, wherein the computer system scans for the wireless network for a predetermined media access control (MAC) address and obtains an Internet Protocol (IP) address associated with a MAC address of the portable wireless endoscope system;
establishing a wireless connection to the computer system, wherein the wireless connection comprises a secure connection with the computer system and the wireless endoscope system, enabling the computer system to execute commands on the wireless endoscope system;
after the computer system initiates a video streaming service, receiving from the computer system one or more instructions over the wireless connection to begin streaming video by the wireless endoscope system;
obtaining, via the digital camera, video imagery via an endoscope optically connected to the endoscope coupler, the video imagery including multiple frames;
analyzing each of the multiple frames of the obtained video imagery, and adjusting one or more characteristics of a frame;
creating modified video data of the adjusted one or more frames; and
streaming to the computer system, via the wireless transceiver, the modified video data;
wherein the wireless endoscope system is configured to receive a stop command from either the computer system or an input via the wireless endoscope system, the stop command stopping the streaming of the video stream from the wireless endoscope system to the computer system;

wherein the wireless endoscope system is configured to receive a start command from either the computer system or an input via the wireless endoscope system, the start command starting the streaming of the video stream from the wireless endoscope system to the computer system;

after stopping the video streaming service, creating by the wireless endoscope system a video file and transmitting the video file from the wireless endoscope system to the computer system, wherein the video file includes multiple frames from the video stream; and after the video file has been transmitted to the computer system, deleting the video file from a storage system of the wireless endoscope system.

2. The system of claim 1, wherein the onboard processor is further configured to perform the operations comprising:
receiving from the computer system, via the wireless transceiver, instructions to initiate a video streaming service on the endoscope system; and
based on the received instructions, starting the video streaming service.

3. The system of claim 1, wherein the onboard processor is further configured to perform the operations comprising:
receiving a start command from the computer system to begin obtaining video imagery;
based on the received command starting image acquisition by the camera of endoscope system;
receiving a stop command from the computer system to stop obtaining video imagery; and
based on the received stop command stopping image acquisition by the camera.

4. The system of claim 1, wherein the onboard processor is further configured to perform the operations comprising:
creating a video file having multiple frames of the modified video data;
determining whether a frame of the video file includes any imagery outside of a patient's body; and
if the frame is determined to include imagery outside of a patient's body, then deleting the frame.

5. The system of claim 1, wherein the onboard processor is further configured to perform the operations comprising:
controlling a light source to illuminate an endoscope optically coupled to the wireless endoscope system.

6. The system of claim 5, wherein the onboard processor is further configured to perform the operations comprising:
determining an average luminosity across multiple pixels of a frame; and
adjusting power being passed to the light source to increase or decrease the luminosity of the light source to a predetermined luminosity value or range.

7. The system of claim 2, wherein the onboard processor is further configured to perform the operations comprising:
establishing a connection with the computer system, where the computer system has determined the IP address of the endoscope system.

8. The system of claim 1, wherein the computer system is configured to perform the operations comprising:
initializing a 3-dimensional (3D) position of the handheld body;
monitoring the rotation of the hand-held body in at least an x-axis, y-axis and a z-axis; and
providing an alert where the rotation of the hand-held body rotates greater than a predetermined threshold angular value.

9. The system of claim 1, wherein the onboard processor is further configured to perform the operations comprising:
determining whether the endoscope system has required versions of software packages installed on the endoscope system; and
automatically updating or installing required versions of the software packages.

10. A computer-implemented method for streaming endoscopic video data comprising:
creating, by a wireless endoscope system, a wireless network for connection by a computer system, wherein the computer system scans for the wireless network for a predetermined media access control (MAC) address and obtains an Internet Protocol (IP) address associated with a MAC address of the portable wireless endoscope system;
establishing, by the wireless endoscope system, a secure wireless connection to the computer system, wherein the wireless connection comprises a secure connection with the computer system and the wireless endoscope system, enabling the computer system to execute commands on the wireless endoscope system;
after the computer system initiates a video streaming service, receiving from the computer system one or more instructions over the secure wireless connection to begin streaming video by the wireless endoscope system;
obtaining, via a digital camera, video imagery via an endoscope optically connected to an endoscope coupler, the video imagery including multiple frames;
analyzing each of the multiple frames of the obtained video imagery, and adjusting one or more characteristics of a frame;
creating modified video data of the adjusted one or more frames; and
streaming to the computer system, via a wireless transceiver, the modified video data;
wherein the wireless endoscope system is configured to receive a stop command from either the computer system or an input via the wireless endoscope system, the stop command stopping the streaming of the video stream from the wireless endoscope system to the computer system;
wherein the wireless endoscope system is configured to receive a start command from either the computer system or an input via the wireless endoscope system, the start command starting the streaming of the video stream from the wireless endoscope system to the computer system;
after stopping the video streaming service, creating by the wireless endoscope system a video file and transmitting the video file from the wireless endoscope system to the computer system, wherein the video file includes multiple frames from the video stream; and
after the video file has been transmitted to the computer system, deleting the video file from a storage system of the wireless endoscope system.

11. The method of claim 10, further comprising:
receiving from the computer system, via the wireless transceiver, instructions to initiate a video streaming service on the endoscope system; and
based on the received instructions, starting the video streaming service.

12. The method claim 10, further comprising:
receiving a start command from the computer system to begin obtaining video imagery;

based on the received command starting image acquisition by the camera of endoscope system;

receiving a stop command from the computer system to stop obtaining video imagery; and based on the received stop command stopping image acquisition by the camera.

13. The method of claim 10, further comprising:

creating a video file having multiple frames of the modified video data;

determining whether a frame of the video file includes any imagery outside of a patient's body; and if the frame is determined to include imagery outside of a patient's body, then deleting the frame.

14. The method of claim 10, further comprising:

controlling a light source to illuminate an endoscope optically coupled to the wireless endoscope system.

15. The method of claim 14, further comprising:

determining an average luminosity across multiple pixels of a frame; and adjusting power being passed to the light source to increase or decrease the luminosity of the light source to a predetermined luminosity value or range.

16. The method of claim 11, further comprising:

establishing a connection with the computer system, where the computer system has determined the IP address of the endoscope system.

17. The method of claim 10, further comprising:

initializing a 3-dimensional (3D) position of the hand-held body;

monitoring the rotation of the hand-held body in at least an x-axis, y-axis and a z-axis; and providing an alert where the rotation of the hand-held body rotates greater than a predetermined threshold angular value.

18. The method of claim 10, further comprising:

determining whether the endoscope system has required versions of software packages installed on the endoscope system; and automatically updating or installing required versions of the software packages.

* * * * *